US00PP13710P39

(12) United States Plant Patent
Mukherjee et al.

(10) Patent No.: US PP13,710 P3
(45) Date of Patent: Apr. 8, 2003

(54) GLADIOLUS HYBRID PLANT NAMED 'TUSHAR MAULI'

(75) Inventors: Devashish Mukherjee, Himachal Pradesh (IN); Devendra Dhayani, Himachal Pradesh (IN); Jaichand Rana, Simla (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 09/815,396

(22) Filed: Mar. 22, 2001

(65) Prior Publication Data

US 2002/0138888 P1 Sep. 26, 2002

(51) Int. Cl.[7] ..... A01H 5/00
(52) U.S. Cl. ..... Plt./301

(58) Field of Search ..... Plt./301

(56) References Cited

U.S. PATENT DOCUMENTS

PP2,666 P * 8/1966 Walker et al. ..... Plt./301

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

The invention relates to a new and distinct Gladiolus hybrid plant named 'Tushar Mauli' characterized by its attractive standard type white color flowers with Neyron Rose edges having a greenish color throat with purple tinge and ruffled petals.

1 Drawing Sheet

BOTANICAL NAME

The present invention relates to a new Gladiolus sp. plant in the family Iridaceae. The name of the new variety is 'TUSHAR MAULI'.

BACKGROUND OF THE INVENTION

The present invention relates to a new and distinct variety of Gladiolus named 'TUSHAR MAULI', a member of the Gladiolus genus. The new variety is the hybrid between the Gladiolus plants 'Oscar' (unpatented) and 'Friendship Pink' (unpatented). 'TUSHAR MAULI' is entirely different in color than its parents, having white (near 158C) ruffled petals with Neyron Rose (near 56A) edges and a greenish-purple (near 80D) ting in the throat. 'Oscar' is Turkey Red, with a blotched sulfur yellow throat, while 'Friendship Pink' is Dawn Pink with a blotched pea green throat having splashes of Ruby Red.

Gladiolus is one of the important cut flowers throughout the world. The commercial cultivation is wide spread in temperate, tropical and subtropical climates. The demand of new varieties with better color, quality flowers, and planting materials is always existing and rising in the floriculture trade.

Applicants initiated a breeding program to develop better types of Gladiolus hybrids suitable to wide range of climatic conditions, and having wide range of characteristics such as better color, increased number of florets and spike length as per the international standards, better yield of corm and cormels, tolerant to the common diseases etc.

Accordingly, applicants initiated a breeding program involving hybridization of commonly available Gladiolus plants in the fields at Institute of Himalayan Bioresource Technology, Palampur, India, in order to develop new and distinct varieties of Gladiolus plants. In other words, the hybrids were developed by crossing parental genotypes involving asexual hybridization in the breeding program.

The program yielded a number of hybrid plants out of which one genotype namely IHBT-GH-381 was selected and named 'TUSHAR MAULI'. This plant was found to have new color, flower size, number of florets per spikes, length of flower spikes, better yield of corms and cormels and less prone to common diseases. Growing the plant on a commercial scale offers the horticulturists an improved and new variety, which can be commercially cultivated.

FIELD OF THE INVENTION

The present invention relates to a new Gladiolus hybrid plant named 'Tushar Mauli' and belonging to the family Iridaceae. The new variety is propagated vegetatively by corms and hence can be maintained as a stable genotype. The plant of the new variety is an ornamental plant widely cultivated for its beautiful flowers which are of commercial and export value.

SUMMARY OF THE INVENTION

The present invention provides a new and distinct hybrid Gladiolus plant named 'TUSHAR MAULI' characterized by its attractive standard type white color flowers with Neyron Rose edges having a greenish color throat with purple tinge and ruffled petals.

BRIEF DESCRIPTION OF ILLUSTRATION

The accompanying photographic illustration shows a typical specimen of the new variety, of field grown flower spike of IHBT-GH-381 ('TUSHAR MAULI') depicting standard type flowers of White (near 158C) with Neyron Rose (near 56A) edges and having a greenish with purple (near 80D) colored tinge. The color chart used to provide the color designations was The R.H.S. Colour chart published by The Royal Horticultural Society, London, United Kingdom.

DESCRIPTION OF THE NEW VARIETY

The new variety provides a new and distinct Gladiolus genotype named as 'TUSHAR MAULI'. This plant has been developed through planned breeding experiments conducted at Institute of Himalayan Resources, (IHBT) Palampur, Himachal Pradesh, India with defined aim to develop superior Gladiolus genotypes. For this purpose, Gladiolus varieties were collected from different sources and grown in the field at Palampur, India for facilitating breeding program. The emasculation and pollination in different varieties were carried out during the months of April and May 1991. The seeds were collected between July and August 1991 and sown in beds under open field conditions and covered with dry grasses in about December 1991. The resultant seedlings were space planted in the field at Palampur in March and April 1992. The corm and cormels of survived hybrid plants were replanted continously four years for screening and multiplication.

Based on superior performance for attractive color combination, compactness of flower spikes, number of flowers per spikes, length of flower spikes, number of flowers remains open at a time, number of corm and cormel production per plant, the plant of this invention (IHBT-GH-381) was selected for further observation and evaluation.

Considering the superior characteristics like excellent color, number of flowers, compactness of flower spikes, plant height, ruffled-ness of flower petals, regeneration potential and freedom from common diseases, it was asexually reproduced through corms and cormels to maintain purity.

The selected hybrid IHBT-GH-381 was named 'TUSHAR MAULI' and grown at row distance of about 1 feet and plant to plant about 6 inches for four consecutive years to study its growth and flowering performance and multiplication. Data was recorded on randomly selected twenty plants every year. The hybrid IHBT-GH-381 maintained uniformity in its growth and flowering performance.

EVIDENCE OF UNIFORMITY AND STABILITY

The new variety has remained stable and uniform for its morphological characters and showed consistency in performance for various growth and flowering parameters during evaluation and vegetative multiplication since 1992. Throughout the evaluation period of the new variety no variants were found from the normal population. The plant shown in the illustration and described below was grown under open field conditions in Palampur area of Himachal Pradesh. The altitude of Palampur is 1300 m above main sea level, which comes under sub-humid, sub-temperate zone, having an average maximum and minimum temperature of 30° C. and 10° C., respectively. The avearage annual rainfall is 250 cm (approximately).

OBJECTIVE DESCRIPTION OF THE GENOTYPE 'TUSHAR MAULI'

The following is an objective description of the new variety.

Genus: Galdiolus.
Species: Hybrid.
Family: Iridacae.
Common name: Sward lily/Gladiolus.
Average plant height: About 159.84 cm.
Growth habit: Erect, uniform.

*Vigor.*—The average growth of the plant during the growth period, i.e., from March to June (from sprouting of the bulbs to the end of flowering), is 158.79 cm. Plant height was recorded from ground level to the bottom of the last flower bud; the average is based on data collected over 5 years.

*Average stem diameter.*—About 1.41 cm.

*Average number of leaves/plant.*—About 7.98.

*Average height of leaves.*—About 70.01 cm.

*Arrangement, form and color of leaves.*—Leaves cauline, alternately overlapped, sheathed; blades cuneate at the base, flattened, linear, lanceolate, acute or acuminate, variable in shape and size; margin entire, thick, fibrous; venation parallel, strong, prominent, veins white; both surfaces glabrous, ventral surface dark green (near 137B), dorsal surface less dark green; leaves 45.5 to 92.4 cm long from ground level (average length is 69.12 cm), width is 2.8 to 6.6 cm (average is 5.09 cm).

*Bud size and color.*—Buds are 5.92 cm to 8.02 cm long (bottom 3 buds were taken) and the average size 6.83 cm long. The diameter of the lower 3 buds ranges from 1.07 cm to 1.44 cm and the average is 1.25 cm. The color of bud is near 1D.

*Average days to flower.*—About 101 days.

*Type of flowers.*—Standard.

*Average number of spikes/plant.*—About 1.42.

*Average length of the flower spike.*—About 141 cm.

*Average number of flowers/spike.*—About 17.90.

*Flower color.*—White near 158C, with Neyron Rose near 56A edges having a greenish with purple near 80D tinge colored throat.

*Type of tepals.*—Ruffled.

*Tepals.*—Perianth petaloid, actinomorphic, 6 tepals arranged in two whorls, 3 each in inner and outer whorls, polyphyllous; tepals stalked, stalk 1 to 1.5 cm long, stalk fused at the base; tepals cuneate or cordate to sub-cordate, the base, apex obtuse or blunt, oblong oblanceolate to lanceolate, margin entire, oblique, lobes 3.5 to 5.5 cm in width, 5.5 to 8.5 cm in length.

*Androecium.*—Stamens 3, triandrous, epiphyllous, adnate to tepals at the base, shorter than tepals; arranged alternate in one whorl; filaments white, slightly curved, about 3.5 to 4 cm long; anther bi-lobed, anther lobe purple brown, 1.5 to 2 cm long, anther extrose, basifixed.

*Gynoecium.*—Ovary inferior, tricarpellary, trilocular, many ovules in each locule, axile placentation; style single, terminal, erect, 6.5 to 7 cm long; stigma 3 lobed, rarely 4 lobed, petaloid, shortly stalked, lobes 6 to 8 mm long, folded, white, lobe margin wavy, shining.

*Average number of flowers remains open at a time.*—About 7.44.

*Average longevity of the 1st flower.*—About 3.52 days.

*Average diameter of 1st flower.*—About 13.3 cm.

*Average longevity of the spike.*—About 11.8 days.

*Average number of corms/plant.*—About 1.55

*Average diameter of corms.*—About 6.77 cm.

*Average number of cormels/plant.*—About 239.

*Commercial propagation.*—Gladiolus plant is commercially propagated vegetatively through corms and cormels. The average diameter of the corm of 'TUSHAR MAULI' is 6.77 cm and the number of cormels/plants is 239.

*Fragrance.*—'TUSHAR MAULI' is not a fragrant hybrid.

*Plant disease resistance or susceptibility.*—Some incidence of Fusarium rot was noticed in the field as well as in the storage. This may be due to the high rainfall during the crop development period, because crop remains in the field during monsoon. But this variety 'TUSHAR MAULI' is performing better than many other gladiolus varieties such as 'Hunting Song' (unpatented), 'Fidelio' (unpatented), 'Her Majesty' (unpatented), 'Oscar', 'Red Beauty' (unpatented), etc., in this region in respect of disease incidence.

We claim:

1. A new and distinct Gladiolus plant named 'TUSHAR MAULI' substantially as herein described and illustrated.

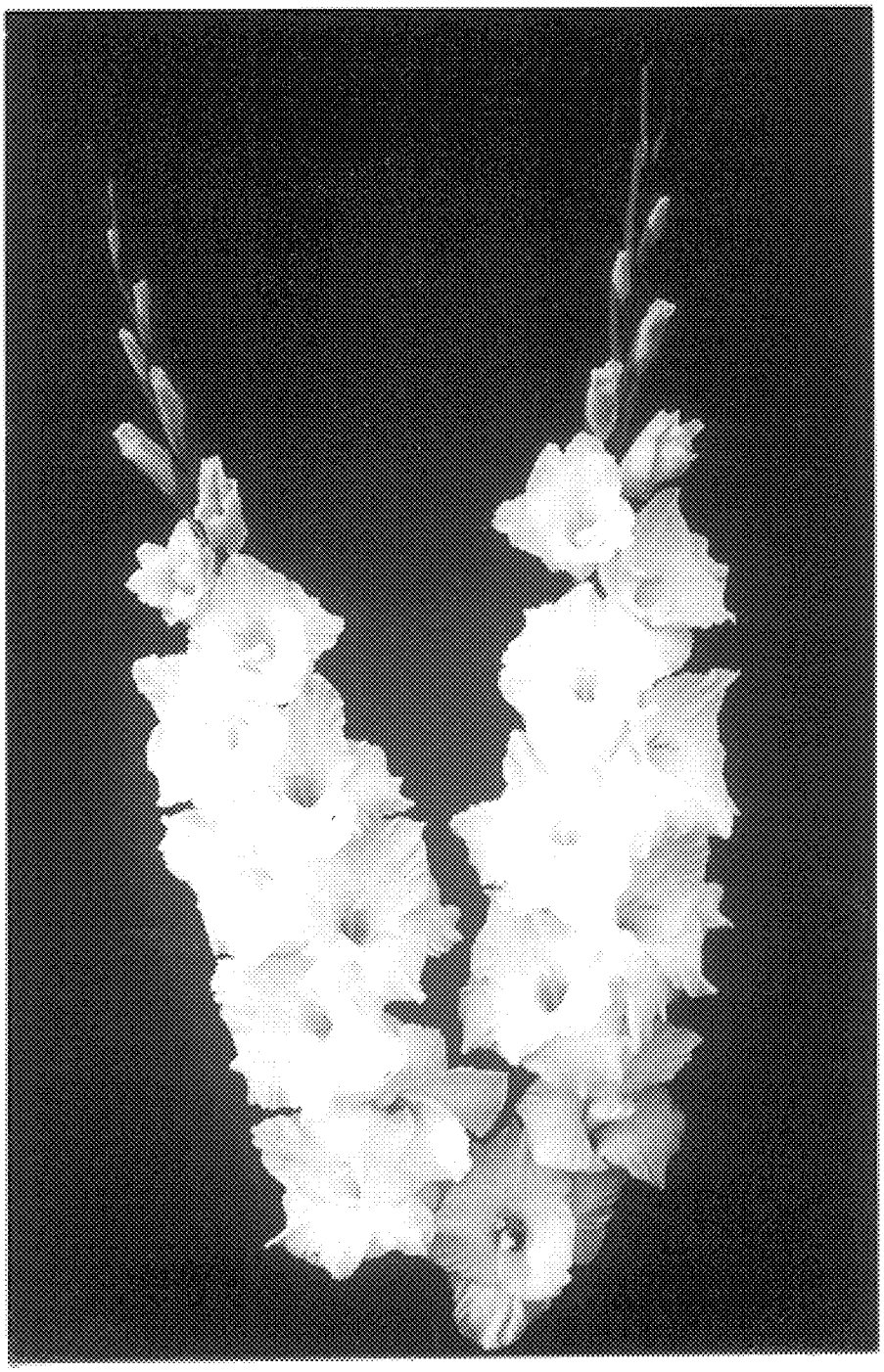

* * * * *